(12) United States Patent
Okuno

(10) Patent No.: US 11,406,684 B2
(45) Date of Patent: *Aug. 9, 2022

(54) FINE NANO-SIZED MEDICINAL AGENT AND USE THEREOF

(71) Applicant: Tetsuji Okuno, Tokyo (JP)

(72) Inventor: Tetsuji Okuno, Tokyo (JP)

( * ) Notice: Subject to any disclaimer, the term of this patent is extended or adjusted under 35 U.S.C. 154(b) by 610 days.

This patent is subject to a terminal disclaimer.

(21) Appl. No.: 16/328,348

(22) PCT Filed: Aug. 25, 2017

(86) PCT No.: PCT/JP2017/030525
§ 371 (c)(1),
(2) Date: Feb. 26, 2019

(87) PCT Pub. No.: WO2018/038253
PCT Pub. Date: Mar. 1, 2018

(65) Prior Publication Data
US 2021/0283060 A1 Sep. 16, 2021

(30) Foreign Application Priority Data

Aug. 26, 2016 (JP) .............................. JP2016-165996

(51) Int. Cl.
| | |
|---|---|
| *A61K 38/17* | (2006.01) |
| *A61P 9/00* | (2006.01) |
| *A61P 29/00* | (2006.01) |
| *A61P 35/00* | (2006.01) |
| *A61K 45/06* | (2006.01) |
| *A61K 45/00* | (2006.01) |
| *A61K 39/395* | (2006.01) |
| *C07K 16/28* | (2006.01) |
| *C07K 14/705* | (2006.01) |
| *A61K 9/16* | (2006.01) |
| *A61K 31/138* | (2006.01) |
| *A61K 31/282* | (2006.01) |
| *A61K 31/337* | (2006.01) |
| *A61K 31/407* | (2006.01) |
| *A61K 31/513* | (2006.01) |
| *A61K 31/593* | (2006.01) |
| *A61K 31/69* | (2006.01) |
| *A61K 31/704* | (2006.01) |
| *A61K 31/7068* | (2006.01) |
| *A61K 35/36* | (2015.01) |
| *A61K 38/14* | (2006.01) |
| *A61K 38/36* | (2006.01) |
| *A61K 9/00* | (2006.01) |

(52) U.S. Cl.
CPC ........ *A61K 38/1774* (2013.01); *A61K 9/0024* (2013.01); *A61K 9/1688* (2013.01); *A61K 31/138* (2013.01); *A61K 31/282* (2013.01); *A61K 31/337* (2013.01); *A61K 31/407* (2013.01); *A61K 31/513* (2013.01); *A61K 31/593* (2013.01); *A61K 31/69* (2013.01); *A61K 31/704* (2013.01); *A61K 31/7068* (2013.01); *A61K 35/36* (2013.01); *A61K 38/14* (2013.01); *A61K 38/1793* (2013.01); *A61K 38/366* (2013.01); *A61K 39/395* (2013.01); *A61K 39/3955* (2013.01); *A61K 45/00* (2013.01); *A61K 45/06* (2013.01); *A61P 9/00* (2018.01); *A61P 29/00* (2018.01); *A61P 35/00* (2018.01); *C07K 14/70503* (2013.01); *C07K 14/70521* (2013.01); *C07K 16/2803* (2013.01); *C07K 16/2818* (2013.01); *C07K 2317/76* (2013.01)

(58) Field of Classification Search
CPC .... A61K 38/1774; A61K 45/06; A61K 45/00; A61K 39/395; A61K 39/3955; A61K 9/1688; A61K 31/138; A61K 31/282; A61K 31/337; A61K 31/407; A61K 31/513; A61K 31/593; A61K 31/69; A61K 31/704; A61K 31/7068; A61K 35/36; A61K 38/14; A61K 38/1793; A61K 38/366; A61K 9/0024; A61P 9/00; A61P 29/00; A61P 35/00; C07K 16/2818; C07K 14/70521; C07K 14/70503; C07K 16/2803; C07K 2317/76
See application file for complete search history.

(56) References Cited

U.S. PATENT DOCUMENTS

| | | | | |
|---|---|---|---|---|
| 6,096,331 | A * | 8/2000 | Desai | A61K 9/0019 424/422 |
| 2008/0020052 | A1 | 1/2008 | Li et al. | 424/490 |
| 2009/0117177 | A1 | 5/2009 | Rapoport et al. | 424/450 |
| 2010/0215751 | A1 | 8/2010 | Desai et al. | 424/489 |
| 2013/0209523 | A1 | 8/2013 | Ichikawa et al. | 424/400 |
| 2013/0287688 | A1 | 10/2013 | Jain et al. | 424/9.1 |
| 2015/0202291 | A1 * | 7/2015 | Bosch | C07K 16/2818 424/156.1 |

FOREIGN PATENT DOCUMENTS

| | | | |
|---|---|---|---|
| CN | 105030682 | * | 11/2015 |
| EP | 2937080 | | 10/2015 |

(Continued)

OTHER PUBLICATIONS

English language translation of Okuno, Tetsuji "Tokushu Gan Chiryo to Kekkannai Chiryo Gan no Kobetsuka Iryo to, Kekkannai Chiryo no Hatasu Yakuwari", Togo Iryo de Gan ni Katsu, 2014 75: 17-20.

(Continued)

*Primary Examiner* — Shirley V Gembeh
(74) *Attorney, Agent, or Firm* — Licata & Tyrrell P.C.

(57) ABSTRACT

The purpose of the present invention is to provide a novel medicinal agent that is therapeutically more effective than conventional medicinal agents. The purpose is achieved by providing a fine nano-sized medicinal agent in which an active ingredient dispersed in a solvent has an average particle diameter of 1-20 nm.

5 Claims, 2 Drawing Sheets

(56) References Cited

FOREIGN PATENT DOCUMENTS

| | | | |
|---|---|---|---|
| JP | 2002-507976 A | | 3/2002 |
| JP | 2002507976 | * | 3/2002 |
| JP | 2008-513381 A | | 5/2008 |
| JP | 2008-542293 A | | 11/2008 |
| JP | 2010-529025 A | | 8/2010 |
| JP | 2014-505666 A | | 3/2014 |
| TW | 201417842 | | 5/2014 |
| WO | 1999/000113 A1 | | 1/1999 |
| WO | 2008/154368 | | 12/2008 |
| WO | 2010/053101 | | 5/2010 |
| WO | 2011/005886 | | 1/2011 |
| WO | 2012/068531 | | 5/2012 |
| WO | 2014/055426 | | 4/2014 |
| WO | 2015/038993 A1 | | 3/2015 |
| WO | 2015/195889 | | 12/2015 |

OTHER PUBLICATIONS

Kunjachan, Sijumon et al. "Nanoparticle mediated tumor vascular disruption: a novel stragety in radiation therapy" NANO Letters 2015 15:7488-7496.
Okuno, Tetsuji "Tokushu Gan Chiryo to Kekkannai Chiryo Gan no Kobetsuka Iryo to, Kekkannai Chiryo no Hatasu Yakuwari", Togo Iryo de Gan ni Katsu, 2014 75: 17-20.
Extended European Search Report in EP17843729.9 dated Apr. 21, 2020.

\* cited by examiner

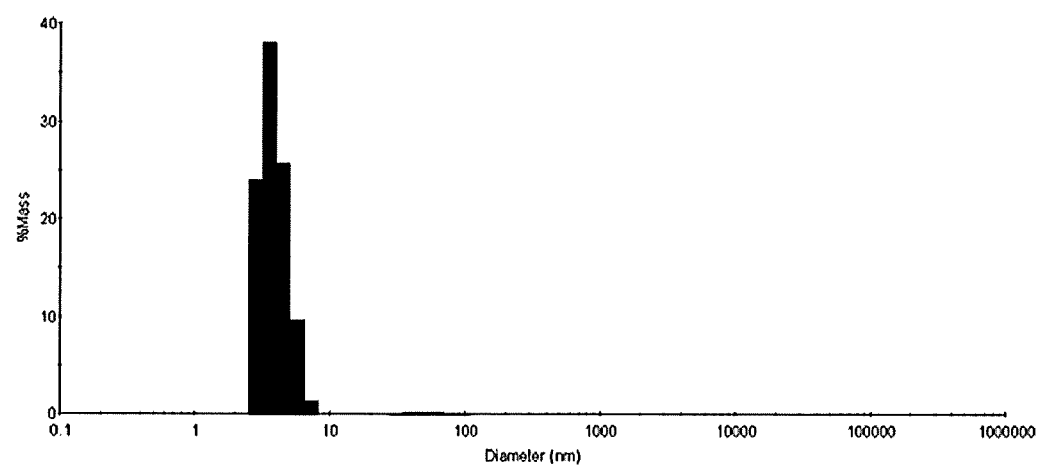
[Fig. 1]

[Fig. 2]
A.
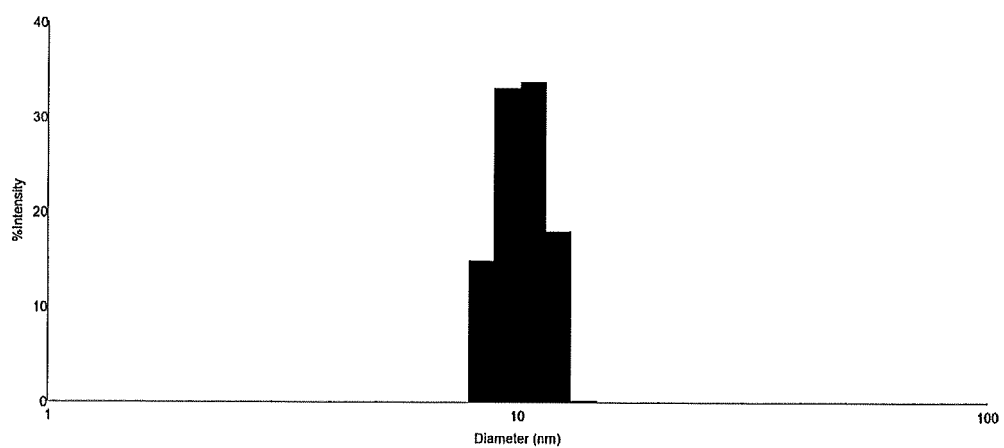
B.
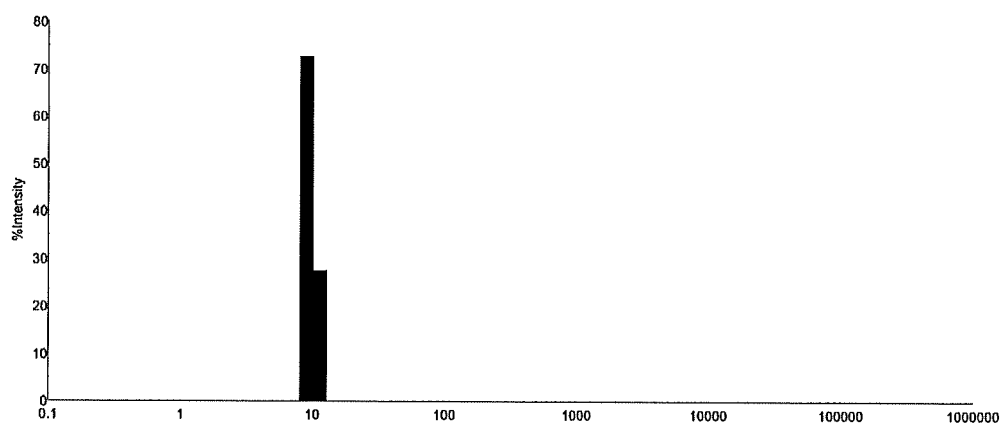

FINE NANO-SIZED MEDICINAL AGENT AND USE THEREOF

TECHNICAL FIELD

The present invention relates to a fine nano-sized medicinal agent having an active ingredient with an average diameter of 1-20 nm when dispersed in a solvent, to the use of the medicinal agent as a microvascular blood flow decreasing agent, and to a method of treating tumors and/or inflammatory diseases using the medicinal agent.

BACKGROUND ART

Cancer cells and stromal cells in cancer tissue secrete angiogenic factors such as vascular endothelial growth factor (VEGF), and within the tissue form new vascular networks arborizing from existing vascular system. It is considered that these new vascular networks provide nutrients necessary for the growth of the cancer tissue and provide pathways for metastasis. Here, for the purpose of preventing nutrient supply from these tumor blood vessels to cancer tissue, attention has been payed to therapies for inhibiting tumor angiogenesis or for embolizing blood vessels and the like, and drugs for embolizing small vessels have been developed.

However, it is difficult to selectively embolize only tumor blood vessels because they form fine vascular networks as mentioned above. Therefore, the method adopted in many cases is to inhibit nutritional transmission by embolizing the original vessel from which tumor vessels arborize. However, this method requires embolizing normal blood vessels and it is therefore concerned that there may be some influence on normal tissue.

In recent years, methods for delivering a drug to a specific part of a tissue have been attracting attention. This method, in which tumor site is specified by e.g., angiography, and a micro-catheter is inserted into the artery that is responsible for the nutrient supply to that tumor part, and a drug such as an anti-cancer agent is administrated through that micro-catheter, is called superselective intraarterial infusion, which is capable of selective delivery of drugs at high concentration to specific site with less side effects as compared to systemic chemotherapy and therefore is considered to have a high efficacy.

Thus, endovascular therapy using a medical equipment inserted into a blood vessel has been drawing attention as being capable of obtaining high efficacy with minimal invasion. However, therapeutic methods to various microvasculature including tumor vessels are in fact yet to sufficiently be in practical use in clinical application.

In recent years, with an application of superselective intraarterial infusion, methods for embolizing blood vessels by administering embolic agents into tumor blood vessels and supporting vessels thereof have been discovered. For example, Patent Reference 1 describes a microsphere vascular embolic agent containing paclitaxel, which is an anti-cancer agent. One purpose of the same agent is to physically embolize blood flow which circulates through tumor blood vessels and therefore the particle diameter of the agent is described to be 100-350 μm in its dry state.

PRIOR ART REFERENCES

Patent References

[PATENT REFERENCE 1] JP A 2008-513381

SUMMARY OF THE INVENTION

Problem to be Solved by the Invention

The present invention aimed to provide a novel medicinal agent having particularly high cell permeability.

Means to Solve the Problem

While the inventor was investigating endovascular therapy using superselective intraarterial infusion which enables a site-specific delivery of anti-cancer agents, it was found that when gemcitabine hydrochloride (Gemzar) dispersed (dissolved) in saline and ammonium glycyrrhizinate are mixed together, an agent having an average particle diameter of about 60-120 nm is formed, and such an agent is highly effective in decreasing blood flow through tumor blood vessels and decreasing the density of tumor blood vessels. It was assumed that this effect was resulted from a small particle diameter of the anti-cancer agent which enables the agent to pass through vascular wall of tumor blood vessels and to readily reach tumor tissues. Based on such findings, the inventor further continued the investigation into an agent which is used in endovascular therapy for cancer, and found that making the particle diameter of an agent even smaller enables the agent to be delivered into tumor cells and furthermore into the nucleus of tumor cells, and as a result, the agent exerts better therapeutic effect, for example, when it is used as a microvascular blood flow decreasing agent, it decreases the density of tumor blood vessels further, etc. and came to complete the present invention.

Namely, the present invention relates to those listed below:

(1) A fine nano-sized medicinal agent, in which an active ingredient dispersed in a solvent has an average particle diameter of 1-20 nm.
(2) The fine nano-sized medicinal agent according to (1), wherein the particle size distribution of the active ingredients dispersed in the solvent is 1 to 20 nm in diameter.
(3) The fine nano-sized medicinal agent according to (1) or (2), wherein the fine nano-sized state of the said agent is prepared by irradiating radiation.
(4) The fine nano-sized medicinal agent according to any one of (1) to (3), wherein the active ingredient is an anti-cancer agent.
(5) The fine nano-sized medicinal agent according to any one of (1) to (4), wherein the agent is a blood flow decreasing agent for tumor vessels or blood vessels at an inflammation site.
(6) The fine nano-sized medicinal agent according to (5), wherein the active ingredient comprises an immune checkpoint inhibitor.
(7) A method for processing a medicinal agent to a fine nano-sized state, wherein the method comprises irradiating the agent with radiation at 100 to 200 μSv/h for 10 to 60 minutes.
(8) The method according to (7), wherein the radiation is emitted from uranium ore as a radiation source.
(9) The method according to (7) or (8), wherein the agent is a nano-sized anti-cancer agent.
(10) The method according to (9), wherein the nano-sized anti-cancer agent comprises a mixture of gemcitabine hydrochloride and glycyrrhizic acid.

EFFECTS BY THE INVENTION

Provided by the present invention is a novel agent having high cell permeability. Owing to its extremely smaller particle diameter compared to conventional agents, the agent of the present invention can pass through cell surface membranes and even nuclear membranes, and thus is highly effective for cells in particular. Such an agent suitably exerts its effect especially when it is used in combination with an agent which is aimed to decrease blood flow through microvasculature, in particular, tumor blood vessels or blood vessels at a site of inflammation.

In diseases having microvasculature, especially in tumor sites, vascular networks are complicated by over-developed microvasculature, causing the congestion of blood stream due to an increased blood flow, leading to hypoxic state at disease sites. However, the agent of the present invention can selectively decrease blood flow through microvasculature, resolve the blood stream congestion and improve the hypoxic state around microvasculature. By improving the hypoxic state, the niche of cancer stem cells is deprived, which in turn suppresses the growth of cancer cells and as a result, the cancer can be treated. Since such a mechanism exerts its effect independent of the type of the organ which develops cancer, it can establish a method of treatment which is equally effective to any cancer.

BRIEF DESCRIPTION OF DRAWINGS

FIG. 1 shows the measurement result of particle size distribution of fine nano-sized medicinal agent made by irradiating the nano-sized anti-cancer agent with radiation. The top graph is a graph showing the particle size distribution of the particles, and the bottom table is peak data. A peak, which was present at Peak 2 position (near 60 nm) before the exposure to radiation shifted to Peak 1 (near 4 nm) after the exposure to radiation.

FIG. 2 is a graph showing the result from measurement of particle diameter of the fine nano-sized immune checkpoint inhibitors. A shows the measurement result of particle size distribution of fine nano-sized CBT agent A, and B shows the measurement result of particle size distribution of fine nano-sized CBT agent B, respectively.

MODES FOR PRACTICING THE INVENTION

Hereinbelow, the present invention will be illustrated in details.
Fine Nano-Sized Medicinal Agent of the Present Invention The present invention provides a fine nano-sized medicinal agent having an active ingredient with an average particle diameter of about 1 to 20 nm when dispersed (dissolved/suspended) in a solvent.

In the present invention, "a medicinal agent" means a specific active ingredient (compound) which elicits a specific pharmacological effect, but may mean an agent (composition) which comprises the active ingredient.

In the present invention, "an fine nano-sized medicinal agent" means the medicinal agent having a small particle diameter so that it shows higher cell permeability than conventional medicinal agents, and includes, but not limited to, for example, a medicinal agent having its particle diameter of less than 40 nm. The fine nano-sized agents may achieve a smaller particle diameter by being dispersed (dissolved/suspended) in a solvent alone or in combination with other ingredients, or may be processed to make the particle diameter smaller after being dispersed (dissolved/suspended) in a solvent. To make a particle diameter smaller, any usual methods in the art can be used, for example, such as shaking, dilutions and stirring.

In the present invention, "microvasculature" means blood vessel(s) which constitutes a microvascular network that is developed de novo in specific disease site. Characteristics of microvasculature include its disorder and congestion relative to normal blood vessels, the presence of a number of arteriovenous shunts, and high permeability at vascular wall. Examples of microvasculature include, though not being limited thereto, such as, for example, a tumor vessel, a blood vessel at an inflammation site, a blood vessel around an ischemic site, and a blood vessel at a site having prolonged pain. In one embodiment of the present invention, microvasculature is preferably a tumor vessel or a blood vessel at an inflammation site, more preferably a tumor vessel.

In the present invention, a "tumor vessel" means a blood vessel which has typically been arborized de nova from existing blood vessel and which constitutes a disorderly and congested vascular network having many arteriovenous shunts observed in a tumor tissue. A tumor vessel is principally formed by angiogenic factors secreted by tumor cells and stromal cells in tumor tissue such as vascular endothelial growth factor (VEGF), has an instable structure with high permeability. This blood vessel not only supplies oxygen and nutrients to tumor cells, but also is involved in hematogenous metastasis.

In the present invention, a "blood vessel at an inflammation site" means a neovessel induced by inflammatory cytokines produced at an inflammation site, and typically includes a blood vessel that constitutes a vascular network developed de nova in rheumatic synovial membrane, for example.

In the present invention, a "blood vessel at a site having prolonged pain" means, in a pathologic condition diagnosed as osteoarthropathy, tendinosis or fasciitis, with chief complaint of chronic pain lasting for 3 months or longer, a blood vessel developed de nova in fascia, tendon or adipose tissue, etc. in a site having pain. Although these vessels would not indicate abnormal vascular density as clear as that in the vessels in tumor or inflammation site, there will be recognizable increase in vascular density accompanied with early venous visualization if observed well.

In the present invention, a "microvascular blood flow decreasing agent" means an agent that, upon being introduced into a microvasculature, has an effect of decreasing the amount of blood flow of said microvasculature. In one embodiment of the present invention, the decrease in the amount of blood flow can be caused by microvascular embolization. In another embodiment, the decrease in the amount of blood flow can be caused by microvascular destruction. Therefore, a microvascular blood flow decreasing agent includes, though not being limited thereto, such as, for example, a substance which embolizes a blood vessel, a substance which inhibits angiogenesis, and a substance which leaks from a blood vessel and decreases blood flow. A microvascular blood flow decreasing agent may be used in combination with another agent. For example, it may be used in combination with, e.g., an anti-cancer agent and anti-inflammatory agent, though not being limited thereto.

The present invention is based on the new finding that by fixing the size of particle diameter of medicinal agent, such as an anti-cancer agent, when dispersed in a solvent, for example less than 40 nm, but is not limited to, the agent elicits higher drug efficacy than that of a conventional active ingredient. Accordingly, the fine nano-sized medicinal agent of the present invention can be used at lower dosage compared to conventional medicinal agents containing equivalent active ingredients.

The reason why the fine nano-sized agent of the present invention shows the high drug efficacy is not fully understood. Not being bound by any theory, but the reasons contemplated can be, for example, the improvement in the affinity of drug to cell surface receptors by having smaller a particle diameter, etc.

In one embodiment of the present invention, an average particle diameter of active ingredients of the fine nano-sized medicinal agents is 1-20 nm. In one preferred embodiment, the particle size distribution of active ingredients of the fine nano-sized medicinal agents is 1-20 nm when dispersed in a solvent. "An average particle diameter" used herein means the distribution range of diameter of all the particles dispersed in a solvent. In one preferred embodiment of the present invention, an average particle diameter or particle size distribution is 1-10 nm. In one further preferred embodiment, an average particle diameter or a particle size distribution is 2-6 nm.

As mentioned above, a fine nano-sized medicinal agent of the present invention may achieve the small particle diameter by being dispersed in a solvent or may be processed to make the particle diameter smaller after being dispersed in a solvent. As a process of making a particle diameter to a fine nano-size, any usual methods in the art, for example, such as shaking, diluting and stirring, can be used, but one preferred embodiment includes a method using radiation hormesis effect by irradiating with radiation as a method for nano-sizing (making an agent fine nano-sized). For example, the small particle size distribution can be achieved by placing a uraninite ore which emits y ray at around 100-200 pSv/h in the vicinity of a container which contains a medicinal agent to be nano-sized, and leaving these for 10-30 minutes.

In nature, the fine nano-sized medicinal agent of the present invention are more readily uptaken by cells compared to an agent with a larger particle size distribution, hence it can suitably be used in pharmaceutical preparations for a variety of applications. An active ingredient which can be used as a pharmaceutical preparation includes, but not limited to, for example, an anti-cancer agent, anti-inflammatory agent, antibody agent, or bisphoshonic acid salt. In one preferred embodiment, the active ingredient is an anti-cancer agent. As mentioned above, the fine nano-sized medicinal agent of the present invention will exert its effect at a smaller dosage compared to that of general medicinal agents, thus is able to reduce the risk of side effects and the like even when used for systemic administration.

In one embodiment of the present invention, the fine nano-sized medicinal agent can be used as a microvascular blood flow decreasing agent. In microvasculature, the permeability of vessel walls tends to be enhanced and hence especially the fine nano-sized medicinal agent of the present invention can suitably be used. The microvasculature to which the microvascular blood flow decreasing agent of the present embodiment can be applied includes, but not limited to, for example, tumor blood vessels, blood vessels at a site of inflammation. Especially preferred are tumor blood vessels.

When using the fine nano-sized medicinal agent of the present invention as a tumor blood flow decreasing agent, the active ingredient include, for example, an anti-cancer agent and immune checkpoint inhibitor and the like.

Anti-cancer agents, which are used as a tumor blood flow decreasing agent preferably include a nano-sized anti-cancer agent and the like. In the present specification, "nano-sized" refers to a medicinal agent having a particle size distribution of about 60-120 nm, which is achieved by being dispersed in a solvent alone or in combination with other ingredients or by being processed to make a particle diameter smaller after being dispersed in a solvent. Examples of nano-sized anti-cancer agent include, but not limited to, gemcitabine hydrochloride (Gemzar) and a mixture of ammonium glycyrrhizinate (G-G emulsion) in addition to a mixture of G-G emulsion and other anti-cancer agents such as adriamycin, oxaliplatin or bleomycin.

One particularly preferred embodiment of the present invention includes a fine nano-sized anti-cancer agent which is processed from a nano-sized anti-cancer drug such as G-G emulsion using hormsis effects. A particle size distribution of around 2-6 nm can be achieved by placing a uraninite ore, which emits y-ray at around 150 µSv/h in the immediate vicinity of a container which contains a nano-sized anti-cancer agent having its particle size distribution of 60-120 nm, and leaving these for 10-30 minutes.

The immune checkpoint inhibitor that is used in the tumor blood vessel flow decreasing agent of the present invention may be any agent which has been known in the art as an immune checkpoint inhibitor, and includes, though not being limited thereto, such as, for example, an anti-CTLA-4, anti-PD-1, anti-PD-L1, anti-TIM-3, anti-LAG-3, anti-B7-H3, anti-B7-H4, anti-BTLA, anti-VISTA, and anti-TIGIT antibodies. In one embodiment of the present invention, an immune checkpoint inhibitor is preferably an anti-CTLA-4 antibody, an anti-PD-1 antibody and an anti-PD-L1 antibody, more preferably anti-CTLA-4 antibody and anti-PD-1 antibody. Typical anti-CTLA-4 antibodies include ipilimumab, and typical anti-PD-1 antibodies include nivolumab and pembrolizumab, and typical anti-PD-L1 antibodies include atezolizumab and MSB0010718C (avelumab).

In the present invention, "tumor" includes benign tumors and malignant tumors (cancers, malignant neoplasms). Cancer includes tumors of hematopoietic organs, epithelial malignant tumors (carcinomas) and non-epithelial malignant tumors (sarcomas). The agent of the present invention particularly exhibit its therapeutic effect in a cancer having tumor vessels, typically in a solid cancer. Normally when an immune checkpoint inhibitor is used in the treatment of cancer, the cancer which can be treated is limited to cancer in which the corresponding immune checkpoint protein is involved in immune evasion. Nevertheless, when the immune checkpoint inhibitor is used as the tumor vessel blood flow decreasing agent, the cancer which can be treated is not particularly limited. For instance, even when an anti-CTLA-4 antibody is used as the microvascular blood flow decreasing agent of the present invention, the cancer to be treated does not necessarily have to express CTLA-4.

The inventor has found that a particle size distribution of about 10-15 nm can be achieved by preparing a tumor blood vessel blood flow decreasing agent comprised of an immune checkpoint inhibitor in combination with other immune checkpoint inhibitors or an antibody agent such as bevacizumab. Accordingly, another preferred embodiment of the present invention comprises a microvascular blood flow decreasing agent having an immune checkpoint inhibitor as an active ingredient, and more preferably comprises a tumor blood vessel blood flow decreasing agent.

A fine nano-sized medicinal agent of the present invention is dispersed in a solvent thus typically be in a form which can be infused or injected, such as liquid or injection. A solvent which can be used in the fine nano-sized medicinal agent of the present invention can include, but not limited to, any solvents or diluents which are usually used in the art and typically can include water, saline and the like.

Method of the Present Invention for Making a Medicinal Agent Fine Nano-Sized

The present invention, as mentioned above, stems from the new finding that by making a medicinal agent to a fine nano-size, the agent exerts the desired effect at a smaller dosage compared to that of a conventional medicinal agent. Therefore, one aspect of the present invention relates to the method for nano-sizing a medical agent (i.e., making a medicinal agent fine nano-sized).

In particular, a method using radiation hormesis effect is suitably used as the method of the present invention for making a medicinal agent fine nano-sized. The hormesis effect refers to a phenomenon where a substance is toxic when used at a high concentration or in a large amount, but the same substance brings beneficial effect when used at a low concentration or in a small amount, and this effect is also observed in radiation. A radiation source, which emits radiation having hormesis effect, includes, for example, a uraninite ore and the like. The uraninite ore is also suitably used in the method of the present invention for making a medicinal agent fine nano-sized.

The method of the present invention for making a medicinal agent fine nano-sized is typically performed by irradiating the immediate vicinity of a medicinal agent which is to be made to a fine nano-size with radiation at around 100-200 μSv/h for 10-60 minutes. An hourly dose of irradiating radiation is preferably about 100-150 μSv/h, and more preferably about 150 μSv/h. The duration of irradiation is preferably 10-30 minutes.

As mentioned above, it is anticipated that the fine nano-sized medicinal agent of the present invention is particularly highly effective when the said agent is used as a microvascular blood flow agent. Therefore, in one preferred embodiment of the present invention, a medicinal agent to be fine nano-sized is a nano-sized anti-cancer agent. The nano-sized anti-cancer agents typically include, but not limited to, a mixture of gemcitabine hydrochloride and glycyrrhizinate (G-G emulsion), or a mixture of G-G emulsion and other anti-cancer agents and the like.

Method of the Present Invention for Treating Solid Tumor

As mentioned above, the fine nano-sized agent of the present invention can decrease blood flow through microvasculature, and as a result, can decrease the density of microvasculature. Therefore, the fine nano-sized agent of the present invention can suitably be used as a method for decreasing microvasculature blood flow and a method for treating diseases and symptoms where excessive angiogenesis of microvasculature is recognized. That is, the present invention, in one aspect, includes the method for decreasing microvascular blood flow and the method for treating diseases and symptoms, where excessive angiogenesis of microvasculature are recognized using a fine nano-sized medicinal agent of the present invention. Diseases and symptoms which can be treated by the method of the present invention for decreasing microvasculature blood flow include solid tumors, rheumatism, osteoarthropathy with the main complaint of chronic pain which lasts for three months or longer, tendinosis, fasciitis, spinal stenosis and various pain regarded as chronic pain syndrome.

The fine nano-sized medicinal agent of the present invention, when being administered into tumor blood vessels, the agent can suitably be used as a tumor blood vessel blood flow decreasing agent, which decreases blood flow through the said tumor blood vessels, thereby improves the hypoxic state and decreases the density of tumor blood vessels. Therefore, fine nano-sized medicinal agent of the present invention can be used in a method for treating a solid tumor by improving surrounding micro-environment of solid tumor (niche). That is, the present invention, in one preferred aspect, relates to the method for treating solid tumor by decreasing tumor vessel blood flow.

The method of the present invention for treating solid tumor can be performed using a procedure which is generally referred as "endovascular therapy", and comprises introducing the fine nano-sized medicinal agent into the microvascular network of which blood flow to be reduced. As long as the fine nano-sized medicinal agent of the present invention is introduced into the microvascular network, it may be administered locally or systemically. In the present invention, the word "endovascular therapy" unless otherwise described elsewhere, refers to a therapeutic method of treating diseases by administrating such agents, which decrease blood flow of microvasculature. Accordingly, the method of the present invention for decreasing microvascular blood flow and the method for treating diseases and symptoms where excessive angiogenesis of microvasculature is recognized including solid tumor can suitably be used as one embodiment of endovascular therapy.

In one preferred embodiment of the present invention, the fine nano-sized medicinal agent is locally administrated into the microvasculature of interest. Typical methods for local administration include intraarterial injection, and, particularly a method in which a catheter is introduced in the vicinity of the vessel of interest and the drug is directly administrated is preferred. In the method of the present invention, because the target vessel is microvasculature, the catheter used is preferably a microcatheter in order to introduce the catheter in more vicinity of the target vessel. Methods for local administration into microvasculature using microcatheter is known in the art, and include, though not being limited thereto, such as, for example, superselective intraarterial infusion. The dose of the fine nano-sized medicinal agent to be administered will vary depending on the type of the fine nano-sized medicinal agent to be administered, though a skilled person can calculate an appropriate amount.

As mentioned above, the method for treating solid tumor of the present invention decreases blood flow in tumor vessels which deliver nutrients to a solid tumor, decreases tumor vascular density, and thereby treats the solid tumor. Therefore, it can treat any tumor as long as it is a solid tumor which has tumor vessels. Therefore, tumors which can be treated include, though not being limited thereto, such as, for example, head and neck cancer, esophageal cancer, lung cancer, breast cancer, gastric cancer, liver cancer, bile duct cancer, pancreatic cancer, colorectal cancer, kidney cancer, bladder cancer, prostate cancer, testicular cancer, ovarian cancer, cervical cancer, endometrial cancer, malignant lymphoma and sarcoma.

Moreover, as mentioned above, the method for treating solid tumor of the present invention decreases blood flow in tumor vessels, thereby decreases tumor vascular density, and thereby exhibits therapeutic effect. Here, it is known that tumor vessels not only take a role in nutrient delivery to the tumor, but it also takes a role as a gateway for circulating tumor cells (CTCs). The method of the present invention enables blocking this gateway by decreasing tumor vascular density and eliminating tumor vessels, resulting in a decreased number of CTCs. This enables preventing tumor metastasis itself. Therefore, the solid tumor may be either primary or metastatic. According to the present invention, the tumor at metastatic site can be treated by treating the tumor at primary site. The tumor at the primary site can be treated the other way around by treating the tumor at the metastatic site.

WORKING EXAMPLES

The present invention will further be illustrated in detail with reference to following examples, which indicate specific examples of the present invention, but the present invention is not limited thereto.

Example 1. Fine Nano-Sized Anti-Cancer Agent (1) Measurement of the Particle Size Distribution of Nano-Sized Anti-Cancer Agent:

Emulsion was prepared by mixing gemzar (obtained from Eli Lilly Japan Co., LTD.) 200 mg, monoammonium glycyrrhizinate (obtained from Minophagen Pharmaceutical Co., LTD.) 80 mg, and abraxane (obtained from Taiho Pharmaceutical Co., LTD.) 5 mg. Similarly, another mixture was also prepared by adding adriamycin 10 mg instead of abraxane, taxotere 10 mg, oxaliplatin 50 mg, oxaliplatin 50 mg+mitomycin 4 mg, oxaliplatin 50 mg+mitomycin 4 mg+adriamycin 10 mg or bleomycin 15 mg.

The particle size distribution was measured using LS particle size distribution measuring device LS13 320 (manufactured by Beckman Coulter Inc.).

The result is shown in Table 1

TABLE 1

| Cocktail | Average particle diameter (nm) |
|---|---|
| Adriamycin | 82 |
| Taxotere | 60 |
| Oxaliplatin | 62 |
| Abraxane | 62 |
| Oxaliplatin + Mitomycin | 73 |
| Oxaliplatin + Mitomycin + Adriamycin | 89 |
| Bleomycin | 118 |

As shown in Table 1, even though there was some difference depending on agents being mixed, the agents were prepared to have particle size distributions of about 60-120 nm.

(2) Measurement of the Particle Size Distribution of Fine Nano-Sized Anti-Cancer Agents:

A uraninite ore, which emits y-ray at approximately 150 µSv/h, was placed in the immediate vicinity of a container, which contains a nano-sized anti-cancer agent (formulated by adding abraxane 25 mg, maxacalcitol 10 µg, bortezomib 0.35 mg, propranolol 2 mg, neurotoropin 36 NU, etanercept 25 mg and thrombomodulin 3200 U to the cocktail described above (1) with added oxaliplatin 50 mg+mitomycin 4 mg+5-fluorouracil 250 mg instead of abraxane 5 mg). After being left for 30 minutes, the particle size distribution was measured. The measurement of particle size distribution was carried out using DelsaMax Pro (manufactured by Beckman Coulter Inc.). The result is shown in FIG. 1. A peak, which was present at around 60 nm, shifted to around 4 nm after the exposure to radiation.

Example 2. Therapeutic Preparation of Fine Nano-Sized Immune Checkpoint Inhibitor Fine nano-sized immune checkpoint therapeutic (CBT) preparation A was prepared by dispersing (dissolving) nivolumab 20 mg, pembrolizumab 10 mg and bevacizumab 50 mg in 100 ml of saline. Also, fine nano-sized therapeutic CBT preparation B was prepared by dispersing (dissolving) nivolumab 20 mg, pembrolizumab 10 mg and ipilimumab 2 mg in 100 ml of saline. The particle size distribution was measured using DelsaMax Pro (manufactured by Beckman Coulter Inc.) under the conditions shown in Table 2. The result is shown in FIG. 1.

TABLE 2

| Instrument | |
|---|---|
| Serial Number: | 3200-DMP |
| Model: | DelsaMax Pro |
| Pals Firmware Version: | 1.0.2.10 |
| DLS Firmware Version: | 1.1.2.0 |
| Assist Firmware Version: | 1.0.0.9 |
| Instrument Name: | BCI-3200-DMP |
| Laser Wavelength (nm): | 532.0 |
| Has DLS: | Yes |
| Minimum Temperature (C.): | 3.5 |
| Minimum Temperature without N2 (C.): | 20 |
| Maximum Temperature (C.): | 70 |
| Minimum Ramp Rate (C./min): | 0 |
| Maximum Ramp Rate (C./min): | 1.5 |
| Instrument Parameters: Measurements | |
| Collect Data: | DLS Only |
| Acq Time (s): | 5 |
| Read Interval (s): | 1 |
| Number Acq: | 3 |
| Electric Field Frequency (Hz): | 10.0 |
| Voltage Amplitude (V): | 2.5 |
| Collection Period (s): | 15.0 |
| Auto-attenuation: | Yes |
| Attenuation Level (%): | 0 |
| Auto-attenuation Time Limit(s): | 0 |
| Laser Mode: | Normal |
| Set Temp On Connection: | No |
| Set Temp (C.): | 20 |
| Temp Ramp Enabled: | Yes |
| Temp Ramp Rate (C./min): | 1 |

FIG. 2A shows the result of measurements of fine nano-sized therapeutic CBT preparation A, and FIG. 2B shows the result of measurements of fine nano-sized therapeutic CBT preparation B. Fine nano-sized therapeutic CBT preparation A showed its peak at around 13 nm, and fine nano-sized therapeutic CBT preparation B showed its peak at around 12.6 nm.

INDUSTRIAL APPLICABILITY

According to the present invention, it becomes possible to prepare a medicinal agent having particle size distribution on the order of several to ten-odd nm, by administrating such an agent into tumor blood vessels, it becomes possible to have improved pharmacokinetics than that of a conventional medicinal agent, and to bring change in tumor hemodynamics particularly when used as a tumor blood vessel blood flow decreasing agent. Moreover, it has been found that the use of an immune checkpoint inhibitor having a particle diameter in a fine nano-size as an agent for decreasing blood flow of microvasculature including tumor vessels enables a treatment with longer interval as compared to conventional intravenous therapy, which can make substantial contribution to the improvement in QOL for a patient with advanced cancer. Furthermore, in the present invention the agent is principally locally administered and thus can exhibit its effect in smaller amount as compared to that in conventional administration method and therefore can decrease economic burden when an expensive immune checkpoint inhibitor is used.

The invention claimed is:

1. A method of treating tumors and/or inflammatory diseases, said method comprising administering a fine nano-sized medicinal agent in which an active ingredient dispersed in a solvent has an average particle diameter of 1-20 nm, wherein the active ingredient comprises a mixture of gemcitabine hydrochloride and glycyrrhizic acid.

2. The method of claim 1, wherein particle size distribution of the active ingredients dispersed in the solvent is 1 to 20 nm in diameter.

3. The method of claim 1, wherein the fine nano-sized state of the said agent is prepared by irradiating radiation.

4. The method of claim 1, wherein the fine nano-sized medicine agent is obtainable by a method for processing a medicinal agent to a fine nano-sized state, wherein the method comprises irradiating the agent with radiation at 100 to 200 μSv/h for 10 to 60 minutes.

5. The method of claim 4, wherein the radiation is emitted from uranium ore as a radiation source.

* * * * *